(12) United States Patent
Biedermann et al.

(10) Patent No.: US 12,029,452 B2
(45) Date of Patent: Jul. 9, 2024

(54) POLYAXIAL BONE ANCHORING DEVICE AND INSTRUMENT FOR USE WITH THE SAME

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/841,238

(22) Filed: Jun. 15, 2022

(65) Prior Publication Data

US 2022/0378480 A1     Dec. 1, 2022

Related U.S. Application Data

(63) Continuation of application No. 17/397,862, filed on Aug. 9, 2021, now Pat. No. 11,399,874, which is a
(Continued)

(30) Foreign Application Priority Data

Jul. 24, 2015   (EP) ..................... 15178383

(51) Int. Cl.
*A61B 17/70*     (2006.01)
*A61B 17/56*     (2006.01)
*A61B 90/00*     (2016.01)

(52) U.S. Cl.
CPC ...... *A61B 17/7037* (2013.01); *A61B 17/7032* (2013.01); *A61B 17/7076* (2013.01);
(Continued)

(58) Field of Classification Search
CPC ................ A61B 17/7032–17/7037; A61B 17/861–17/862
See application file for complete search history.

(56) References Cited

U.S. PATENT DOCUMENTS 5,882,350 A    3/1999   Ralph et al.
6,248,105 B1   6/2001   Schläpfer et al.
(Continued)

FOREIGN PATENT DOCUMENTS

CN     2803295 Y       8/2006
CN   202637097 U       1/2013
(Continued)

OTHER PUBLICATIONS

Extended European Search Report for EP Application No. 15178383.4, mailed Mar. 31, 2016, 12 pages.
(Continued)

*Primary Examiner* — Julianna N Harvey
(74) *Attorney, Agent, or Firm* — Lewis Roca Rothgerber Christie LLP

(57) ABSTRACT

A bone anchoring device includes a receiving part with a rod receiving portion having a first end, a second end, a recess for the rod, an outer surface, and a first engagement structure on the outer surface that extends farther radially outwardly than other parts of the rod receiving portion, and a flexible head receiving portion for inserting and clamping the head. The bone anchoring device also includes a locking ring configured to be arranged around the head receiving portion for locking the head, the locking ring having an outer surface and a second engagement structure on the outer surface that extends farther radially outwardly than the outer surface of the rod receiving portion. The engagement structures are
(Continued)

configured to be engaged by an instrument to move the locking ring from a locking position to a position where the inserted head is pivotable.

21 Claims, 8 Drawing Sheets

Related U.S. Application Data continuation of application No. 16/284,631, filed on Feb. 25, 2019, now Pat. No. 11,191,572, which is a continuation of application No. 15/217,747, filed on Jul. 22, 2016, now Pat. No. 10,258,383.

(60) Provisional application No. 62/196,739, filed on Jul. 24, 2015.

(52) U.S. Cl.
CPC ...... *A61B 17/7086* (2013.01); *A61B 17/7091* (2013.01); *A61B 2017/564* (2013.01); *A61B 2090/037* (2016.02)

(56) References Cited

U.S. PATENT DOCUMENTS

| | | | |
|---|---|---|---|
| 8,388,659 | B1 | 3/2013 | Lab et al. |
| 8,506,609 | B2 | 8/2013 | Biedermann et al. |
| 8,556,938 | B2 | 10/2013 | Jackson et al. |
| 8,888,827 | B2 | 11/2014 | Harper et al. |
| 8,926,671 | B2 | 1/2015 | Biedermann et al. |
| 8,951,294 | B2 | 2/2015 | Gennari et al. |
| 9,155,567 | B2 | 10/2015 | Auerbach et al. |
| 9,603,627 | B2 | 3/2017 | Krüger |
| 9,839,446 | B2 | 12/2017 | Biedermann et al. |
| 10,271,877 | B2 | 4/2019 | Biedermann et al. |
| 10,426,521 | B2 | 10/2019 | Mosnier et al. |
| 11,399,874 | B2 * | 8/2022 | Biedermann ...... A61B 17/7091 |
| 2006/0173454 | A1 | 8/2006 | Spitler et al. |
| 2007/0167949 | A1 | 7/2007 | Altarac et al. |
| 2008/0015576 | A1 | 1/2008 | Whipple |
| 2009/0149887 | A1 | 6/2009 | Schlaepfer et al. |
| 2010/0114108 | A1 * | 5/2010 | Strauss ............ A61B 17/7076 606/102 |
| 2010/0152787 | A1 | 6/2010 | Walsh et al. |
| 2010/0234902 | A1 | 9/2010 | Biedermann et al. |
| 2011/0276098 | A1 | 11/2011 | Biedermann et al. |
| 2012/0046701 | A1 | 2/2012 | Gennari et al. |
| 2012/0059426 | A1 | 3/2012 | Jackson et al. |
| 2012/0179209 | A1 | 7/2012 | Biedermann et al. |
| 2012/0179211 | A1 | 7/2012 | Biedermann et al. |
| 2013/0079833 | A1 | 3/2013 | Biedermann et al. |
| 2013/0085536 | A1 * | 4/2013 | Biedermann ...... A61B 17/7076 606/328 |
| 2013/0096622 | A1 | 4/2013 | Biedermann et al. |
| 2013/0096623 | A1 | 4/2013 | Biedermann et al. |
| 2013/0110179 | A1 | 5/2013 | Barrus et al. |
| 2014/0012337 | A1 | 1/2014 | Biedermann et al. |
| 2014/0188173 | A1 | 7/2014 | Mishra et al. |
| 2014/0236239 | A1 | 8/2014 | Biedermann et al. |
| 2014/0257411 | A1 | 9/2014 | Rezach |
| 2015/0080960 | A1 | 3/2015 | Biedermann et al. |
| 2015/0134006 | A1 | 5/2015 | Ziolo et al. |
| 2017/0181776 | A1 | 6/2017 | Beretta et al. |
| 2018/0132903 | A1 | 5/2018 | Biedermann et al. |

FOREIGN PATENT DOCUMENTS

| | | |
|---|---|---|
| CN | 103027732 A | 4/2013 |
| CN | 103976785 A | 8/2014 |
| CN | 104434283 A | 3/2015 |
| EP | 2 851 021 A1 | 3/2015 |
| FR | 2 920 663 A1 | 3/2009 |
| WO | WO 2011/077511 A1 | 6/2011 |
| WO | WO 2015/069873 A1 | 5/2015 |

OTHER PUBLICATIONS

European Search Report dated Nov. 17, 2015 for Application No. 15167435.5; (7 Pages).

* cited by examiner

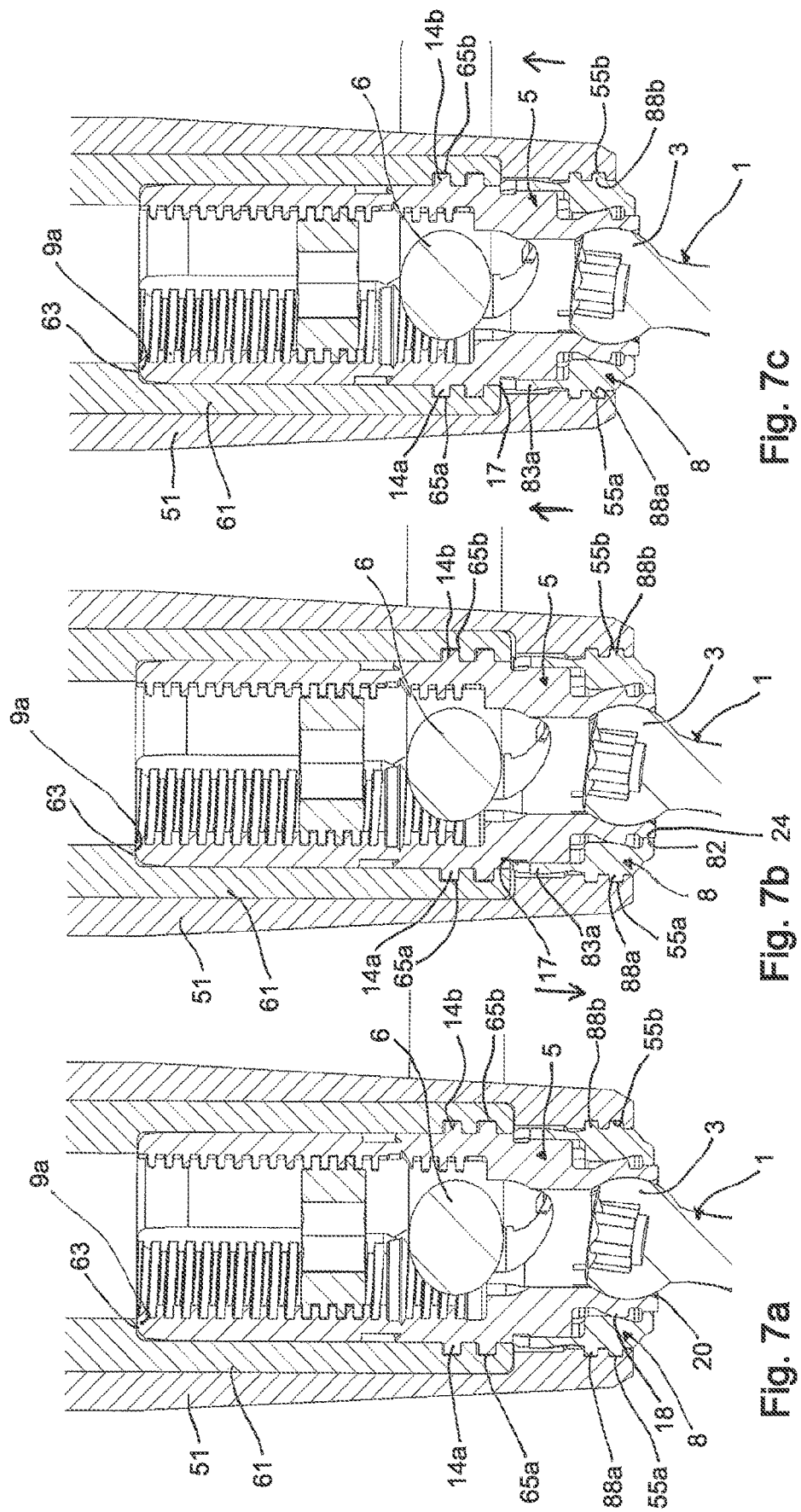

POLYAXIAL BONE ANCHORING DEVICE AND INSTRUMENT FOR USE WITH THE SAME

CROSS-REFERENCE TO RELATED APPLICATION(S)

This application is a continuation of U.S. patent application Ser. No. 17/397,862, filed Aug. 9, 2021, which is a continuation of U.S. patent application Ser. No. 16/284,631, filed Feb. 25, 2019, now U.S. Pat. No. 11,191,572, which is a continuation of U.S. patent application Ser. No. 15/217,747, filed Jul. 22, 2016, now U.S. Pat. No. 10,258,383, which claims the benefit of U.S. Provisional Patent Application Ser. No. 62/196,739, filed Jul. 24, 2015, the contents of which are hereby incorporated by reference in its entirety, and claims priority from European Patent Application EP 15 178 383.4, filed Jul. 24, 2015, the contents of which are hereby incorporated by reference in its entirety.

BACKGROUND

Field

The invention relates generally to a polyaxial bone anchoring device and an instrument for use with the device. More specifically, the bone anchoring device includes a receiving part for coupling a rod to a bone anchoring element, wherein the receiving part has a rod receiving portion for receiving the rod and a head receiving portion for clamping a head of the bone anchoring element, and a locking ring for locking the head in the head receiving portion. The receiving part and the locking ring are configured to be movable relative to each other from a non locking position to a locking position, and vice versa, for example, by using an instrument.

Description of Related Art

US 2011/0276098 A1 describes a polyaxial bone anchoring device including a receiving part for receiving a rod for coupling the rod to a bone anchoring element, the receiving part including a rod receiving portion with a channel for receiving a rod and a head receiving portion that is flexible for clamping a head of the bone anchoring element. A locking ring is configured to be positioned around the head receiving portion. The locking ring can assume a first position where the head receiving portion is expandable to facilitate insertion of the head and a second position in which the locking ring compresses the head receiving portion such that the head is held adjustably at a first angular position relative to the receiving part. Further, the locking ring can assume a third position in which the head is locked in the receiving part. For locking the head, a locking element is used that also locks the rod in the rod receiving portion.

US 2013/0085536 A1 describes a polyaxial bone anchoring device including a receiving part with a rod receiving portion and head receiving portion for introducing and clamping of the head and a locking ring configured to be arranged around the head receiving portion. The locking ring includes an engagement structure for engagement with a tool to allow the locking ring to be moved out of the locking position, i.e. releasing the locking mechanism. This enables a surgeon or other practitioner to carry out revisions or further positioning or re-positioning of the angular position of a receiving part with respect to the bone anchoring element.

SUMMARY

In spinal surgery, often multiple segments of the spinal column have to be corrected and/or stabilized using a spinal rod and polyaxial bone anchors. During such a procedure, repeated adjustments of the bone anchoring elements and the rod relative to the receiving parts of respective polyaxial bone anchoring devices may become necessary.

It is an object of the invention to provide a polyaxial bone anchoring device having an outer locking ring that allows for improved handling during surgery, and to provide an instrument adapted for use with such a polyaxial bone anchoring device.

With such a polyaxial bone anchoring device and instrument, a user can move the locking ring relative to the receiving part from a non locking position where the head is pivotable relative to the receiving part to a locking position where the head is locked, and vice-versa, by displacing an outer tube of the instrument relative to an inner tube of the instrument. The instrument can be used when the rod and a locking element are already inserted into a rod receiving portion of the receiving part, but when the rod is not yet fixed. A temporary locking of the bone anchoring element in the receiving part can be effected using the instrument. Therefore, the locking element is not needed for the temporary locking of the head. As a result, the polyaxial bone anchoring device allows a user to adjust or re-adjust an angular position of the receiving part relative to the bone anchoring element several times while the rod is already inserted.

Moreover, the head of the bone anchoring element can be locked and released relative to the receiving part independently of locking of the rod. Similarly, the rod can also be locked and released independently of locking of the head of bone anchoring element. Therefore, the function of the polyaxial bone anchoring device in combination with the instrument is similar to that of a polyaxial bone anchoring device with an inner compression member and a two-part locking element, wherein the head and the rod can be locked independently.

In a locking position of the locking ring that has been achieved with the aid of the instrument, it is further possible to pull the bone anchoring device with the instrument towards the inserted rod, thereby also pulling the associated vertebra towards the rod, for correcting a position of the corresponding vertebra.

The locking ring can also assume an insertion position for inserting the head of the bone anchoring element into a head receiving portion of the receiving part. The instrument can be used for placing the receiving part with the locking ring in the insertion position onto a head of a bone anchoring element that has already been inserted in bone.

A system including the polyaxial bone anchoring device and the instrument adapted thereto is also provided. Furthermore, the instrument also permits a drive tool to be guided therethrough for tightening the locking element for fixing the rod.

With such a polyaxial bone anchoring device and instrument, various adjustments and re-adjustments of angular positions and/or rod positions can be more easily performed during surgery, without applying larger forces that could result in damage to surrounding material, such as tissue, blood vessels, or nerves. Revisions or secondary adjustments of the rod and the receiving part relative to the bone anchoring element can thus be performed in a more controlled manner.

In addition, with a polyaxial bone anchoring device according to embodiments of the invention, a modular system can be provided that allows for combining of various bone anchoring elements with the receiving part, on demand, depending on the actual clinical requirements in each specific case. This reduces the overall cost of using polyaxial screws, reduces inventory, and gives a surgeon a wider or more versatile choice of implants.

BRIEF DESCRIPTION OF THE DRAWINGS

Further features and advantages of the invention will become apparent from the description of embodiments by means of the accompanying drawings. In the drawings:

FIGS. 7a to 7c show cross-sectional views of steps of actuating the locking ring relative to the receiving part using the instrument, the cross-sections taken in a plane extending through the center of the receiving part and arranged at an angle of about 45° relative to the axis of the inserted rod;

DETAILED DESCRIPTION

Figures 1, 2:
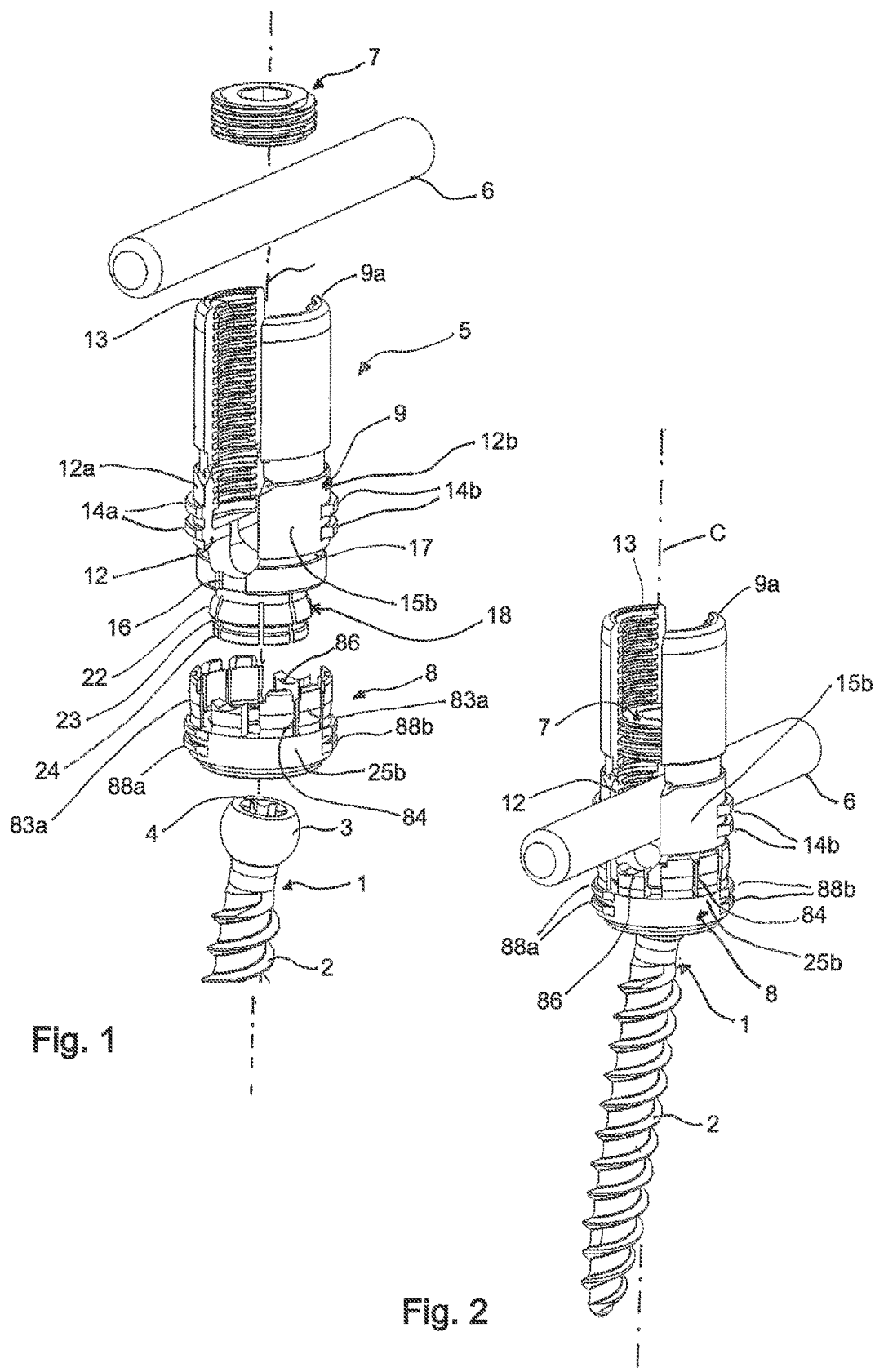
FIG. 1 shows an exploded perspective view of a first embodiment of a polyaxial bone anchoring device.
FIG. 2 shows a perspective view of the polyaxial bone anchoring device of FIG. 1 in an assembled state.
Figure 3:
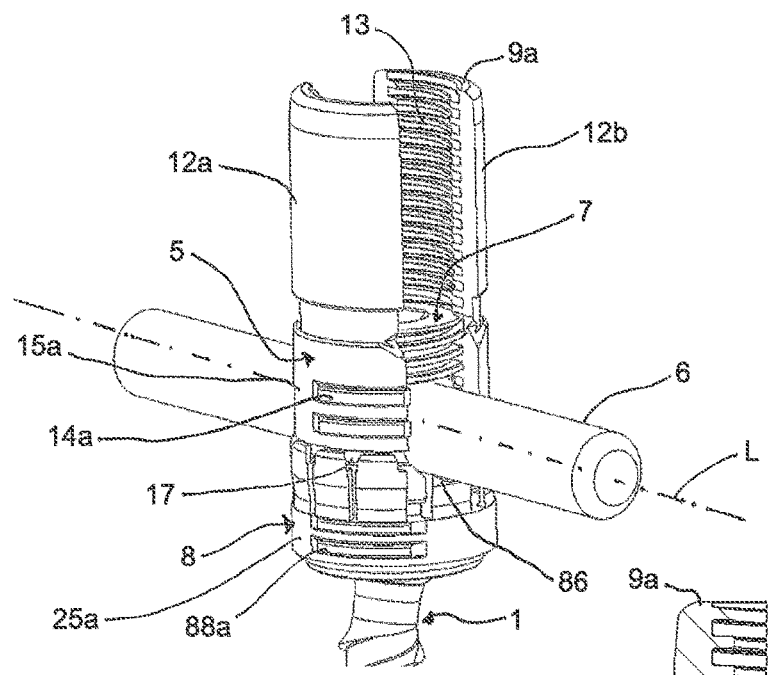
FIG. 3 shows a perspective view of the polyaxial bone anchoring device of FIG. 2 rotated by about 90°.

As shown in FIGS. 1 to 4, a bone anchoring device according to an embodiment of the invention includes a bone anchoring element 1 in the form of, for example, a bone screw having a shank 2 with a threaded portion and a head 3 with a spherically-shaped outer surface portion. The head 3 has a recess 4 for engagement with a driver or tool. The bone anchoring device also includes a receiving part 5 for receiving a rod 6 to be connected to the bone anchoring element 1. Further, a fixation element 7 in the form of, for example, an inner screw or set screw may be provided for fixing the rod 6 in the receiving part 5. In addition, the bone anchoring device includes a locking ring 8 for locking the head 3 in the receiving part 5.

The receiving part 5 has a rod receiving portion 9, which may have an outer shape that is substantially cylindrical. The rod receiving portion 9 has a first end 9a and an opposite second end 9b, and a central axis C that passes through the first end 9a and the second end 9b. The first end 9a may serve as an abutment for a portion of the instrument, as described in greater detail below. A coaxial first bore 10 is provided at the second end 9b, as shown, for example in FIG. 4. A diameter of the first bore 10 is smaller than a diameter of the head 3 of the bone anchoring element 1. The rod receiving portion 9 further includes a coaxial second bore 11 extending from the first end 9a to a distance from the second end 9b. A diameter of the second bore 11 is larger than the diameter of the first bore 10. At a distance from the first end 9a, a circumferential groove 9c is provided that has a lower wall 9c' which extends at an acute angle with respect to the central axis C, or in other words, with respect to a bottom of the groove 9c. At approximately the same axial position, an internal groove 9d is provided that may have a portion with a V-shaped cross-section. At the axial position corresponding to the lower wall 9c' of the groove 9c and to the internal groove 9d, the wall thickness of the rod receiving portion 9 is reduced to provide a break-off area.

A substantially U-shaped recess 12 extends from the first end 9a in the direction of the second end 9b in the rod receiving portion 9, wherein a width of the recess 12 is slightly larger than a diameter of the rod 6, such that the rod 6 can be placed in the recess 12 and can be guided therein. By means of the recess 12, two free legs 12a, 12b are formed, on which an internal thread 13 may be provided. The internal thread 13 can be, for example, a metric thread, a flat thread, a negative angle-thread, a saw-tooth thread, or any other thread form. Preferably, a thread form such as a flat thread or a negative angle thread is used to prevent or reduce splaying of the legs 12a, 12b when the inner screw 7 is screwed-in. A portion of the legs 12a, 12b above the outer groove 9c form extended tabs that can be broken off. The depth of the recess 12 is such that when the rod 6 is placed into the recess 12 and the locking element 7 is screwed between the legs 12a, 12b, the locking element 7 does not substantially protrude out of the receiving part 5 when the extended tabs have been broken off.

At an outer surface of the rod receiving portion 9 an engagement structure for engagement with the instrument is provided, wherein the engagement structure may be formed by a plurality of circumferential ribs 14a, 14b. In the embodiment shown, on each leg 12a, 12b two ribs 14a, 14b, are respectively provided. The ribs 14a, 14b are positioned between the groove 9c and the second end 9b of the rod receiving portion 9. Each of the plurality of ribs 14a, 14b extends over a segment of the circumference of the rod receiving portion 9, for example, for approximately a quarter circle. The arrangement is such that one end of each rib 14a, 14b is positioned at the rod receiving recess 12 and the other end of each rib ends approximately to the middle of each leg 12a, 12b. Hence, in a circumferential direction, there is a rib-free surface portion 15a, 15b on the outer surface of each leg 12a, 12b, where the ribs 14a, 14b are not present. Furthermore, the ribs 14a, 14b are arranged in an asymmetric manner with respect to a plane extending through the central axis C and a longitudinal axis L of the rod receiving recess 12. More specifically, the position of the ribs 14a, 14b is offset by 180° measured in relation to the central axis C, and is rotated with respect to the central axis C such that the ribs 14a of the leg 12a extend to the rod receiving recess 12 at one side of the receiving part 5 and the ribs 14*b* extend to the rod receiving recess 12 at the other side of the receiving part 5. This permits the instrument to be placed first onto the rib-free portions 15*a*, 15*b*, and then to be rotated to engage the ribs 14*a*, 14*b*, as described in greater detail below. The ribs 14*a*, 14*b* may have a substantially rectangular cross-section and may have inclined end portions. It shall be understood that the number of ribs on each leg 12*a*, 12*b* is not limited to two, but one single rib or more than two ribs may be provided on each leg in other embodiments. Also the shape of the ribs may be different in other embodiments.

As can be seen in particular in FIG. 1, cut-outs 16 are provided in the rod receiving portion 9, which extend from the second end 9*b* to the recess 12. The cut-outs 16 are provided on either end of the channel formed by the recess 12.

Meanwhile, the locking element 7, in the form of an inner screw, has a thread corresponding to the internal thread 13 provides on the legs 12*a*, 12*b*.

On an outer surface of the rod receiving portion 9, in the region of the legs 12*a*, 12*b*, a groove 17 may be provided that extends in a circumferential direction and serves for engagement with a portion of the locking ring 8. The groove 17 may be asymmetric to allow for disengagement of the locking ring 8 from the groove 17 when the locking ring 8 is shifted downwards, away from the first end 9*a*.

At the side of the second end 9*b*, the receiving part 5 further includes a head receiving portion 18 providing an accommodation space for the head 3 of the bone anchoring element 1. The head receiving portion 18 has a greatest outer diameter that is smaller than a greatest outer diameter of the rod receiving portion 9. An internal hollow section 19 forms a seat for the head 3 of the bone anchoring element 1, and is open via an opening 20 to a free end 18*b* of the head receiving portion 18. The internal hollow section 19 has a shape adapted to the shape of the head 3. In the embodiment shown, the internal hollow section 19 is a spherical section to accommodate the spherical head 3. Moreover, the hollow section 19 is configured to encompass the head 3 of the bone anchoring element 1 from the side, to cover a region including a largest diameter of the head 3. A plurality of slits 21 are provided in the head receiving portion 18 that are open to the free end 18*b*. The slits 21 render the head receiving portion 18 flexible so that the head receiving portion 18 can be compressed to clamp and lock an inserted head 3 in the hollow internal portion 19 by means of friction. A number and size of the slits 21 is provided depending on the desired flexibility of the head receiving portion 18. The flexibility of the head receiving portion 18 is such that the head 3 of the bone anchoring element 1 can be inserted into the hollow internal portion 19 by expanding the head receiving portion 18, and can be clamped by compressing the head receiving portion 18.

Figure 4:
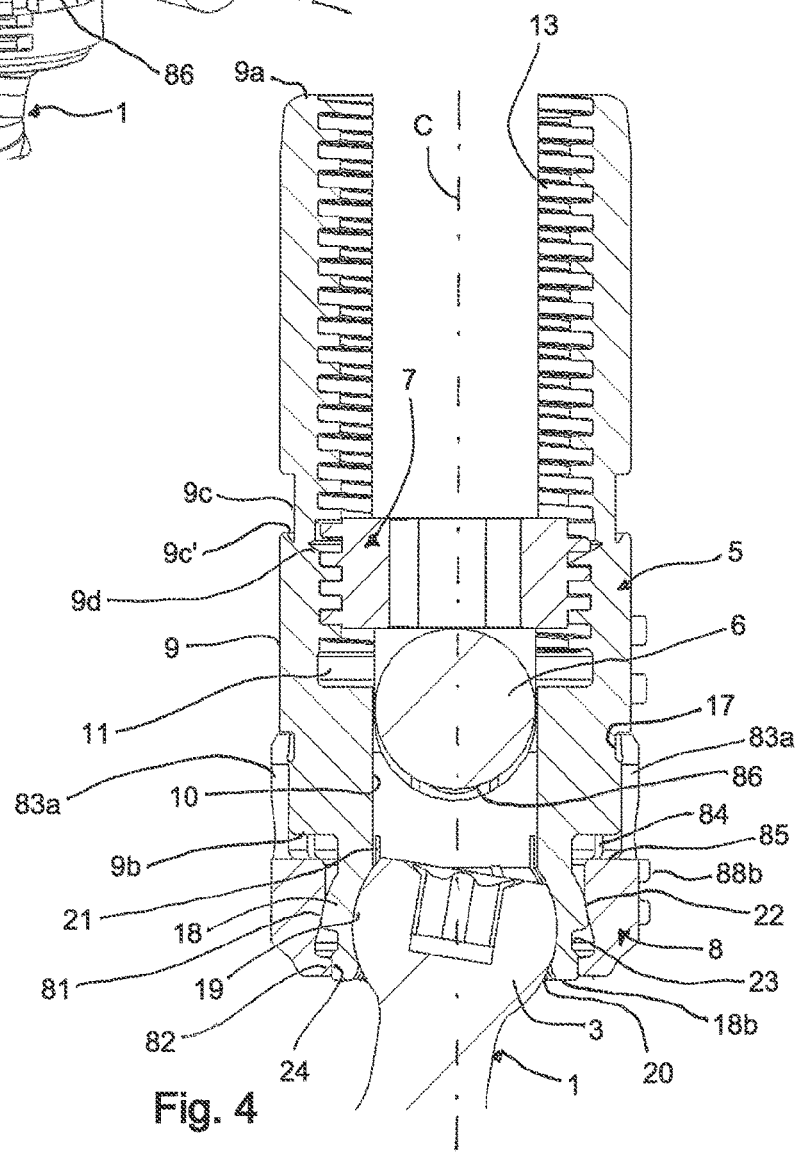
FIG. 4 shows an enlarged cross-sectional view of the polyaxial bone anchoring device of FIGS. 1 to 3, the cross-section taken in a plane perpendicular to an axis of an inserted rod and extending through the center of a receiving part of the bone anchoring device.

As illustrated in particular in FIGS. 1 and 4, an outer surface of the head receiving portion 18 has a first section 22 with an outer diameter that increases towards the free end 18*b*, for example, in an outwardly curved or conically widening manner. Adjacent to the first section 22, there may be a circumferential groove 23 that is recessed with respect to the first section 22 and that serves for engagement with a portion of the locking ring 8. The groove 23 may be shaped so as to allow for disengagement of the locking ring 8 from the groove 23 (i.e., for moving a portion of the locking ring 8 out of the groove 23) when the locking ring 8 is moved in a direction towards the free end 18*b* (or away from the first end 9*a* of the rod receiving portion 9). This is realized, for example, by having a lower wall of the groove 23 that is inclined and widens towards the free end 18*b*. Adjacent to the groove 23, there is a third portion 24 of the head receiving portion 18 with a substantially cylindrical outer surface. The third portion 24 may be configured to cooperate with a portion of the locking ring 8 to enhance a clamping effect of the locking ring 8 on the head receiving portion 18.

The locking ring may 8 include a portion that is substantially cylindrical, and has an upper end and a lower end. In a mounted state, the upper end faces towards the first end 9*a* of the rod receiving portion 9, and the lower end is oriented in the direction of the free end 18*b* of the head receiving portion 18. Approximately in a central region of the locking ring 8, at an inner wall, a first portion 81 is provided that cooperates with the first outer surface portion 22 of the head receiving portion 18 to compress the head receiving portion 18. The first portion 81 may be tapered, straight, or curved, for example, with a curvature directed towards a center of the locking ring 8. At the lower end, there is an inwardly projecting edge 82, an inner diameter of which may be smaller than an inner diameter of other portions of the locking ring 8. The inwardly projecting edge 82 is configured to engage the groove 23 of the head receiving portion 18, and to engage the cylindrical portion 24 of the head receiving portion 18 when the bone anchoring device is in a locked state.

The locking ring also includes upwardly extending wall portions 83*a* that are separated from each other by slits 84. The upwardly extending wall portions 83*a* are arranged at an outer circumference or region of an inner circumferential shoulder 85 of the locking ring 8, and render the upper portion of the locking ring 8 flexible. A number and size of the slits 84 and a thickness of the wall portions 83*a* are configured such that a desired flexibility is obtained. At respective free ends of the wall portions 83*a*, the wall portions 83*a* are configured to engage the groove 17 provided on the outer surface of the rod receiving portion 9.

Two projections 86 that are located diametrically opposite to each other are also formed at the locking ring 8. The projections 86 have a height such that they extend through the cut-outs 16 of the receiving part 5 and project above a bottom of the substantially U-shaped recess 12 when the locking ring 8 is in a position where the shoulder 85 abuts the second end 9*b* of the rod receiving portion 9. A free end surface of the projection 86 forms a rod support surface. The locking ring 8 is arranged around the head receiving portion 18 of the receiving part 5 such that the projections 86 are located at the positions of the recess 12. By means of this, the projections 86 and the cut-outs 16 prevent the locking ring 8 from rotating relative to the receiving part 5 when the rod 6 is not yet inserted in the recess 12.

The locking ring 8 further includes on its outer surface an engagement structure for engagement with the instrument described in more detail below. The engagement structure includes a plurality of ribs 88*a*, 88*b* that are arranged on an outer surface of the locking ring 8 between the flexible wall portions 83*a* and the lower end of the locking ring 8. The ribs 88*a*, 88*b* extend over a segment of an outer circumference of the locking ring 8, for example, for approximately a quarter circle or less than a quarter circle. In the embodiment shown, the ribs include two pairs 88*a*, 88*b* of ribs that are arranged diametrically opposite to one another. Each pair 88*a*, 88*b* includes two axially spaced apart ribs extending in a circumferential direction on each side of the locking ring 8. The position of the ribs in a circumferential direction corresponds to the position of the ribs 14*a*, 14*b* of the rod receiving portion 9 when the locking ring 8 is mounted around the head receiving portion 18 and the projections 86 extend into the cut-outs 16. In other words, one group of ribs 88a extends circumferentially around the locking ring 8 from a circumferential position adjacent to one projection 86 to a certain distance therefrom, and the opposite group of ribs 88b extends circumferentially from a position adjacent to the opposite projection 86 to a certain distance therefrom. By means of this, rib-free surfaces 25a, 25b are formed between the ribs 88a, 88b, that are aligned with the rib-free surfaces 15a, 15b when the locking ring 8 is mounted around the receiving part 5. The ribs 88a, 88b may have substantially rectangular cross-sections and inclined end portions in a circumferential direction. It shall be noted, however, that the shape of the ribs may be different in other embodiments. Also, in other embodiments, there may be one single rib or more than two ribs on each side of the locking ring.

Because the head receiving portion 18 is flexible, the locking ring 8 can be mounted onto the receiving part 5 from the free end 18b of the head receiving portion 18.

In an embodiment of the invention, the locking ring 8 can assume three main positions relative to the receiving part 5. In a first position (not shown), the inwardly projecting edge 82 of the locking ring 8 engages or is positioned adjacent to the groove 23 of the head receiving portion 18. In this position, the head 3 of the bone anchoring element 1 can be inserted into the internal hollows space 19 of the receiving part 5 from the free end 18b of the head receiving portion 18. The locking ring 8 is prevented from moving further upwards towards the first end 9a of the rod receiving portion 9 because the shoulder 85 abuts against the second end 9b of the rod receiving portion 9 in this position. This position may also be referred to as an insertion position.

In a second position, the locking ring 8 is shifted towards the free end 18b of the head receiving portion 18 until the flexible wall sections 83a snap with their free ends into the groove 17 of the rod receiving portion 9. In this position, the head 3 is not yet locked, but may be prevented from removal out of the internal hollow space 19. In some embodiments, the head 3 may also be frictionally clamped in this state to such an extent that the bone anchoring element 1 is still pivotable relative to the receiving part 5 when a force, for example, a manually applied force, is applied to the bone anchoring device to overcome the friction force. This position may also be referred to as a pre-locking position.

In a third position, the locking ring 8 is shifted further towards the free end 18b of the head receiving portion 18 (or away from the first end 9a of the rod receiving portion 9), such that the head 3 is finally locked relative to the receiving part 5. In this position, the head receiving portion 18 is compressed by the locking ring 8, so that the head 3 cannot move and is fixed at an angular position with respect to the receiving part 5. In this position, there is a gap formed between upper ends of the flexible wall sections 83a and the groove 17.

The receiving part 5, the locking ring 8, the locking element 7, and the bone anchoring element 1 may each be made of bio-compatible materials, for example of titanium or stainless steel, of a bio-compatible alloy, such as a NiTi-alloys, for example Nitinol, magnesium or magnesium alloys, or from a bio-compatible plastic material, such as, for example, polyether ether ketone (PEEK) or poly-1-lactide acid (PLLA). In addition, the parts can be made of the same as or of different materials from one another.

Figure 5:
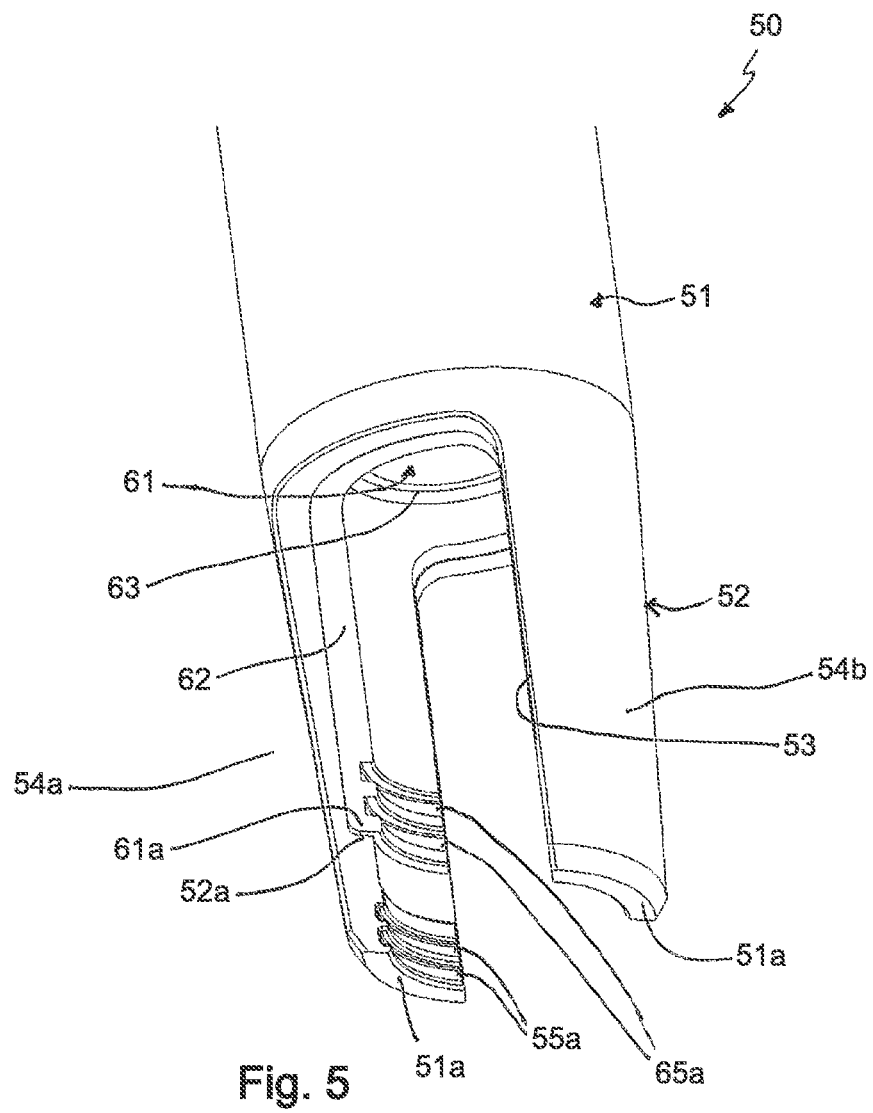
FIG. 5 shows a perspective view of a front portion of an instrument adapted for use with the polyaxial bone anchoring device in FIGS. 1 to 4.

Turning now to FIG. 5, an instrument that is adapted for use with the polyaxial bone anchoring device according to FIGS. 1 to 4 will be described. The instrument 50 includes an outer tube 51 and an inner tube 61, wherein the outer tube 51 and the inner tube 61 are axially displaceable relative to each other along a longitudinal axis of the tubes. Preferably, the outer tube 51 and the inner tube 61 are secured against rotation relative to each other, so that rotating the outer tube 51 also rotates the inner tube 61, and vice-versa. Preferably the axial position of the inner tube 61 relative to the outer tube 51 can be locked. The displacement of the inner tube and the outer tube relative to each other can be effected, for example, by a lever (not shown), such as a toggle lever, whereby a first end of a first lever arm is connected to the outer tube 51 and a first end of a second lever arm is connected to the inner tube 61, and where second ends of the lever arms can be actuated by hand. This is, however, only an example, and any other mechanism for displacing and locking the tubes 51, 61 relative to each other can also be implemented.

The outer tube 51 and the inner tube 61 each has a front portion 52, 62. An outer surface of the front portion 52 of the outer tube may be slightly tapered towards a free end 51a of the outer tube 51. At least the front portion 62 of the inner tube 61 may be guided in the front portion 52 of the outer tube 51. A free end 61a of the inner tube 61 may abut against a circumferentially extending shoulder 52a on an inner wall of the outer tube 51. Further, a recess 53 is formed that extends from the free end 51a of the outer tube 51, and through the front portion 52 of the outer tube 51 and the front portion 62 of the inner tube 61. The recess 53 has an inner diameter or width that is at least as large as an outer diameter of the receiving part 5 in the region of the rib-free surfaces 15a, 15b and as an outer diameter of the locking ring 8 in the region of the rib-free surfaces 25a, 25b, such that the instrument 50 can be placed onto and around the receiving part 5 and the locking ring 8. A length of the recess 53 in an axial direction is such that the receiving part 5 can be accommodated in the front portion 52, 62 of the tubes 51, 61 instrument 50. Thus, the inserted rod 6 can also extend through the recess 53. At a distance from the free end 61a of the inner tube 61, an inner shoulder 63, for example an annular shoulder, is formed, which serves as an abutment for the first end 9a of the rod receiving portion 9 of the receiving part 5. By means of the recess 53, two free legs 54a, 54b are formed on the instrument 50. The shape of the recess 53 is such that the width of the legs 54a, 54b may decrease towards the free end 51a. This facilitates easier finding of the receiving part 5 in-situ, and placing of the instrument 50 onto the receiving part 5 and the locking ring 8 in-situ during surgery.

At a distance from the free end 51a, the outer tube 51 defines circumferentially extending grooves 55a, 55b in an inner wall of the legs 54a, 54b, respectively. The number and shape of the grooves 55a, 55b corresponds to the number and shape of the ribs 88a, 88b of the locking ring 8. In the embodiment shown, two axially spaced apart grooves 55a, 55b are provided on each side. The grooves 55a, 55b are configured to engage the ribs 88a, 88b of the locking ring 8. Similarly, circumferentially extending grooves 65a, 65b are provided at an inner wall of the inner tube 61 at a distance from the free end 61a. The grooves 65a, 65b are configured to cooperate with the ribs 14a, 14b of the rod receiving portion 9. When the inner tube 61 is at an engagement position of the instrument 50, described in greater detail below, the distance between the grooves 55a, 55b of the outer tube 51 and the grooves 65a, 65b of the inner tube 61 corresponds to the distance between the ribs 88a, 88b on the locking ring 8 and the ribs 14a, 14b on the rod receiving portion 9 when the locking ring 8 is in the pre-locking position.

The instrument 50 as a whole, or parts thereof, may be made of one or more of the same materials mentioned above with respect to the polyaxial bone anchoring device.

Figure 6A:
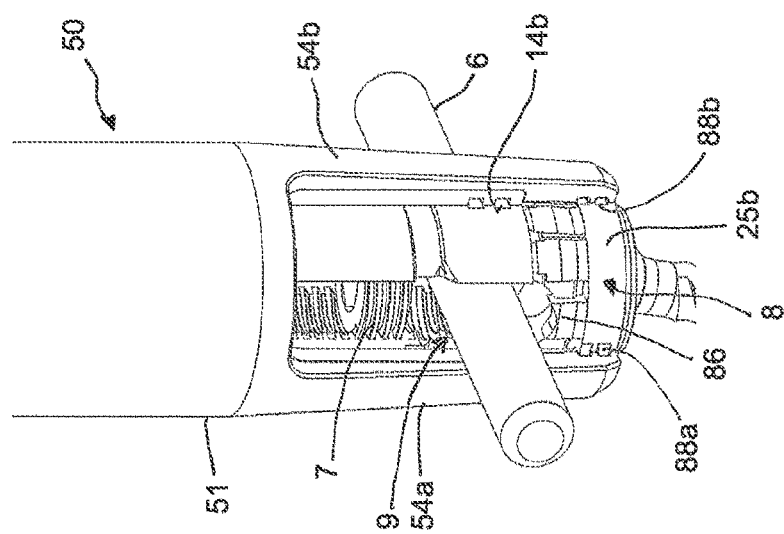
FIGS. 6a to 6c show perspective views of steps of connecting the instrument of FIG. 5 with the polyaxial bone anchoring device of FIGS. 1 to 4.
Figure 6B:
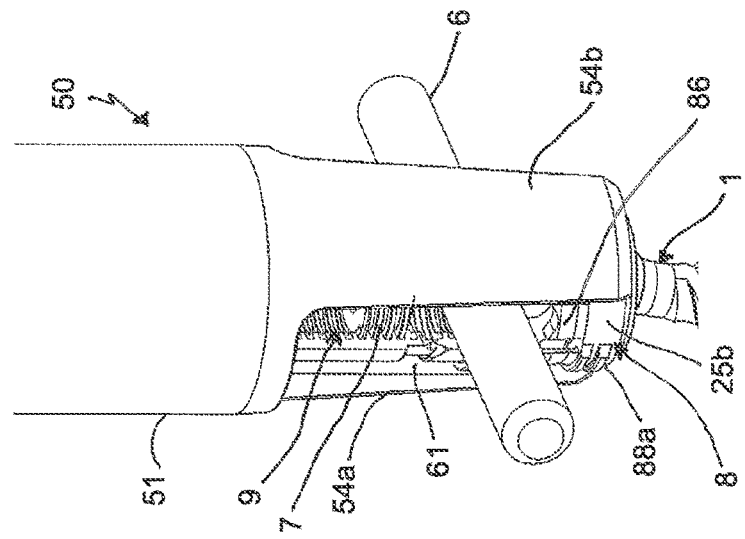
Figure 6C:
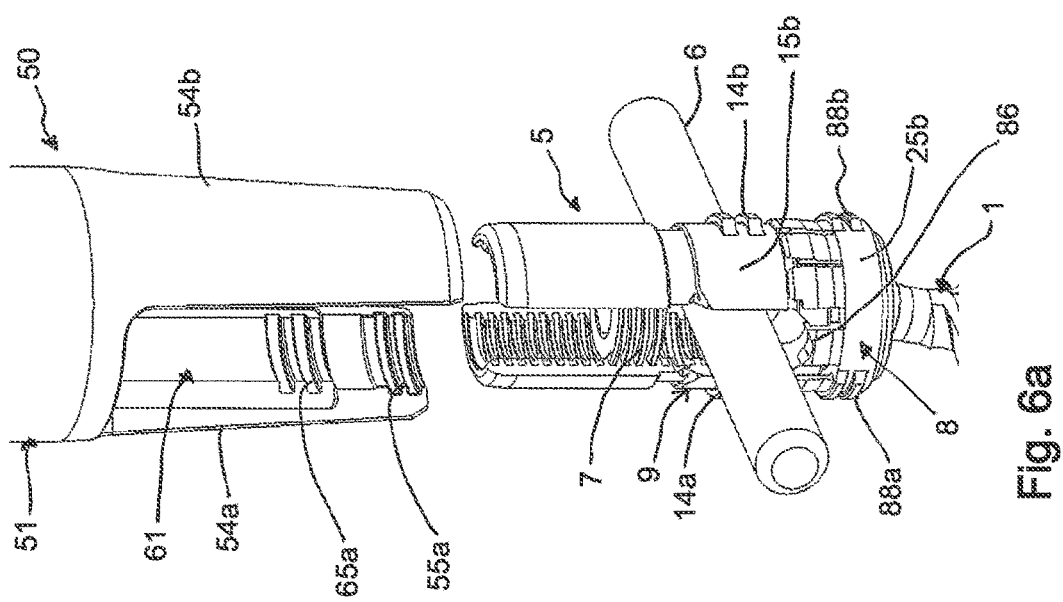
Figure 8:
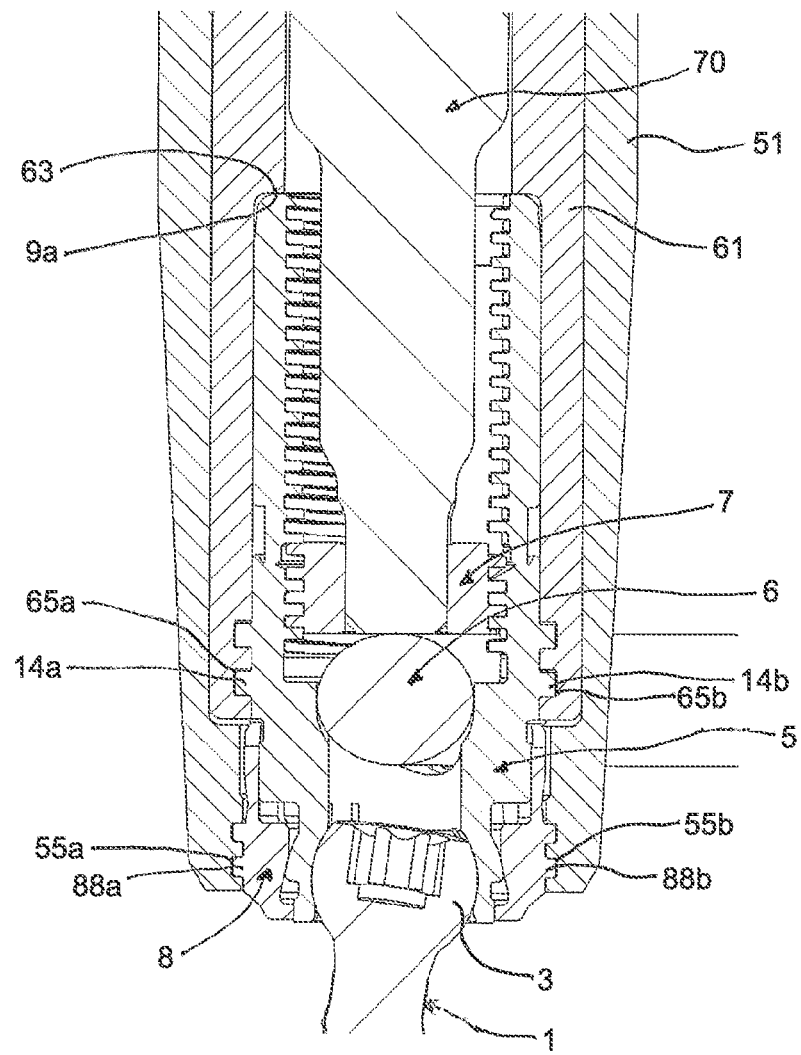
FIG. 8 shows a cross-sectional view of a step of locking a rod in a rod recess of the receiving part using a tool extending through the instrument, the cross-section taken in a plane extending through the center of the receiving part and arranged at an angle of about 45° relative to the axis of the inserted rod.

The operation of the instrument 50 will now be described with reference to FIGS. 6a to 7c. First, FIG. 6a to FIG. 6c show steps of placing the instrument 50 onto the receiving part 5. In FIG. 6a, the bone anchoring element 1 may already be inserted into a bone. The locking ring 8 is in the pre-locking position, where the flexible wall portions 83a abut against an upper wall of the groove 17 of the rod receiving portion 9. The rod 6 and the locking element 7 may already be inserted in the receiving part 5, but the locking element 7 is not tightened so that the rod 6 is still movable along the rod axis and also has some space for moving axially up and down. The front portion of the instrument 50 is oriented such that the legs 54a, 54b are aligned with the rib-free surface portions 15a, 15b of the rod receiving portion 9 and the rib-free surface portions 25a, 25b of the locking ring 8. Then, as depicted in FIG. 6b, the instrument 50 is moved downward relative to the receiving part 5 so that the legs 54a, 54b are placed over the receiving part 5 until the first end 9a of the receiving part abuts against the inner shoulder 63 of the inner tube 61. In this position, the inner grooves 55a, 55b of the locking ring are at a same axial position as the ribs 88a, 88b of the locking ring 8, and the inner grooves 65a, 65b of the inner tube 61 are at a same axial position as the ribs 14a, 14b of the rod receiving portion 9. Therefore, when the instrument 50 is rotated, the grooves 55a, 55b of the outer tube 51 engage the ribs 88a, 88b of the locking ring 8, and at the same time, the grooves 65a, 65b of the inner tube 61 engage the ribs 14a, 14b of the rod receiving portion 9, as shown in FIG. 6c.

The cooperation of the engagement structures in the form of ribs and grooves connects the outer tube 51 to the locking ring 8 and the inner tube 61 to the receiving part 5 in form-fit manners, respectively, such that a force for moving the locking ring 8 relative to the receiving part 5 in an axial direction can be transmitted through the instrument 50.

FIGS. 7a to 7c illustrate the use of the instrument 50 for both locking of the head 3 and releasing the lock on the head 3 relative to the receiving part 5. In FIG. 7a, the locking ring 8 is in the pre-locking position, which means that the flexible wall portions 83a abut against the upper wall of the outer grooves 17 on the rod receiving portion 9. The head 3 is pivotable in the head receiving portion 18, but cannot be pulled out through the lower opening 20. The receiving part 5 is held by the inner tube 61 in a form-fit manner, so that the receiving part 5 cannot move relative to the inner tube 61, at least in an axial direction. The locking ring 8 is engaged by the outer tube 51.

As can be seen further in the figures, an inner diameter of the inner tube 61 above the shoulder 63 is such that the locking element 7 can be inserted through the inner tube 61 and into the rod receiving portion 9 of the receiving part 5.

In the next step, as depicted in FIG. 7b, the outer tube 51 is moved downward relative to the inner tube 61, so that the inner edge 82 of the locking ring 8 presses more against the lower portion 24 of the head receiving portion 18 and the first portion 81 of the locking ring 8 further compresses the first outer surface portion 22 of the head receiving portion 18, to lock the head 3 therein. Meanwhile, the rod is still movable to allow adjustments of the rod position relative to the receiving part 5. In this locking position of the locking ring 8, as shown in FIG. 7b, the instrument 50 can also be used to pull the bone anchoring device towards the inserted rod 6, to correct a position of the associated vertebra.

Next, for performing further adjustments, the lock on the head can be released, as depicted in FIG. 7c. The outer tube 51 can be pulled up until the shoulder 52a abuts against the free end 61a of the inner tube 61. Thereby, the locking ring 8 is moved upward out of the locking position and back into the pre-locking position, which is the same position depicted in FIG. 7a.

With the possibility of locking the head 3 and then also releasing the locked head 3 while the rod 6 and the locking element 7 are already inserted in the receiving part 5, a greater variety of adjustment steps can be carried out, which simplifies the surgical procedure.

Finally, once a correct angular position of the head 3 and a correct position of the receiving part 5 relative to the rod 6 has been found, the locking element 7 can be tightened, for example, with a drive tool 70 that is inserted through the inner tube 61 and that engages the locking element 7. Tightening the locking element 7 moves the rod 6 downwards, which in turn presses the rod 6 onto the rod support surfaces 86 of the locking ring 8 to also move the locking ring 8 down relative to the receiving part 5. Thereby the head 3 and the rod 6 are locked simultaneously by the locking element 7. The instrument 50 can then be removed by rotating the instrument 50 so that the grooves 55a, 55b, disengage from the ribs 88a, 88b, and so that the legs 54a, 54b are aligned with the rib-free surfaces 15a, 15b, 25a, 25b. In this position, the instrument 50 can be pulled away from the receiving part 5. The extended tabs at the first end 9a of the rod receiving portion 9 of the receiving part 5 may be broken off at the end of the procedure.

In a surgical operation, a plurality of bone anchoring devices are connected by the rod. It may be possible to use several instruments 50 for several bone anchoring devices simultaneously, which facilitates the steps such as the adjustment, re-positioning, etc., of each bone anchoring device relative to the rod.

Figure 9:
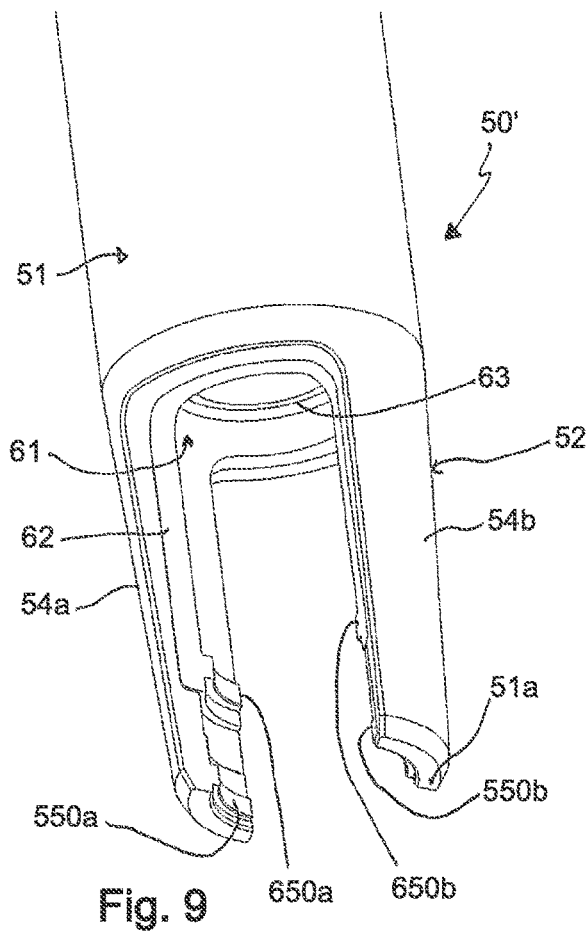
FIG. 9 shows a perspective view of a front portion of a second embodiment of an instrument.
Figure 10:
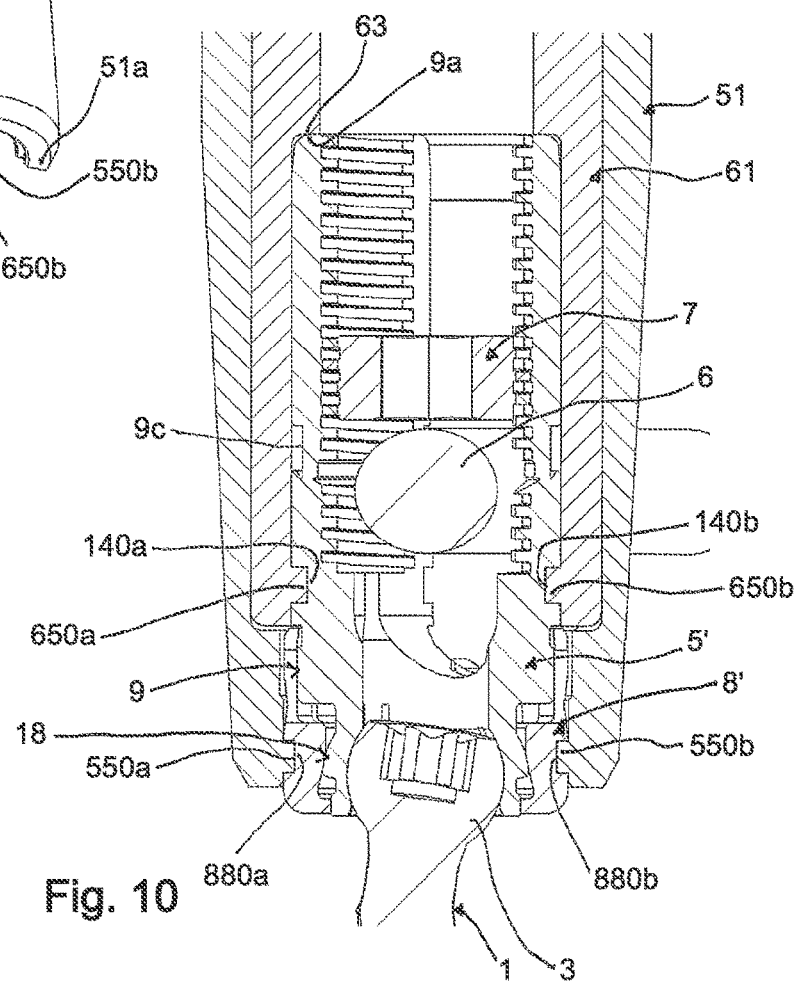
FIG. 10 shows a cross-sectional view of a second embodiment of the polyaxial bone anchoring device with the instrument shown in FIG. 9 attached, the cross-section taken in a plane extending through the center of the receiving part and arranged at an angle of about 45° relative to the axis of the inserted rod.

A further embodiment of a bone-anchoring device and instrument is shown in FIGS. 9 and 10. The embodiment of the bone anchoring device and the instrument in FIGS. 9 and 10 differs from the previous embodiments only in the engagement structures for the instrument and the bone anchoring device. All other parts are the same or similar to the previously described embodiments, and are indicated with the same reference numerals as in the previous embodiments, and their descriptions therefore will not be repeated. The receiving part 5' has in the rod receiving portion 9 a single groove 140a, 140b at an outer wall of each of the legs 12a, 12b. The circumferential extending groove 140a, 140b is located at a distance from the outer groove 9c. The instrument 50' has a corresponding circumferential projection 650a, 650b at an inner wall of the inner tube 61. The inner projection 650a, 650b is at a position and is shaped so as to be able to engage the groove 140a, 140b at the receiving part 5'.

Similarly, a single groove 880a, 880b is provided at an outer surface of the locking ring 8'. A corresponding circumferential rib 550a, 550b is provided at an inner surface of the outer tube 51. The rib 550a, 550b is configured to engage the groove 880a, 880b at the locking ring 8'. Hence, in contrast to the first embodiment, grooves are provided at the receiving part 5' and projections or ribs are provided at the instrument 50'. The function and operation of the parts may be the same as or similar to that of the first embodiment.

Figure 11:
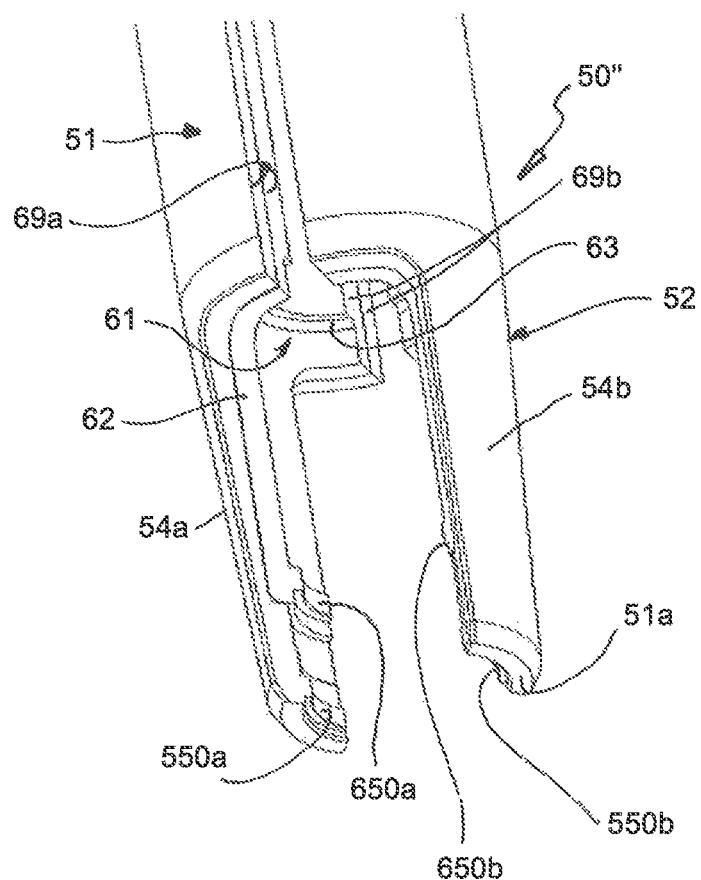
FIG. 11 shows a front portion of a third embodiment of an instrument.

A further modified tool embodiment which facilitates easier outward splaying of the legs 54a, 54b is depicted in FIG. 11. Like numerals denote the same or similar parts as in the previous embodiments. In the instrument 50" shown in FIG. 11, the outer tube 51 and the inner tube 61 are both provided with slots 69a, 69b, which allow legs 54a, 54b to spread apart more easily when the instrument 50" is moved downward relative to the bone anchoring device, similarly as shown in FIGS. 6a and 6b. The circumferential ribs or projections 550a, 550b, 650a, 650b may thus slide over outer surfaces of the receiving part and locking ring, respectively, and snap into or otherwise engage corresponding grooves 140a, 140b, 880a, 880b. Depending on the particular design of the tool and/or the bone anchoring device, a further rotation step for engaging the respective parts may or may not be necessary.

Further modifications can also be contemplated. For example, on each of the receiving part and/or on the locking ring, a combination of ribs and grooves can be provided, and the instrument may have a counterpart or complementary structure, or in other words, a combination of grooves and ribs configured to engage the structures at the receiving part. The shape and the number of the engagement elements may also vary. The ribs and grooves need not extend circumferentially in a plane in some embodiments, but can instead extend along a helix-shape, for example. Therefore, the engagement structures on the instrument, the receiving part, and the locking ring can also be realized with, for example, threads. Other engagement structures may also be contemplated that provide a form-fit connection which can transmit forces onto the bone anchoring device and which can be effected by a rotating and/or sliding movement of the instrument relative to the bone anchoring device. In some embodiments, the engagement structures may also be provided on only one side of the rod receiving portion and one side of the locking ring.

The bone anchoring device according to other embodiments of the invention can be provided in further modified forms. For example, the head of the bone anchoring element can have any other shape, such as, for example, a cylindrical shape, whereby a monoaxial bone screw is provided, allowing rotation of a screw element around a single axis with respect to the receiving part. The head can also be conically shaped or otherwise shaped, with the internal hollow section of the head receiving portion adapted to the specific shape. In a further modification, the flexibility of the head receiving portion may be based on or facilitated by properties of the material, for example, a plastic material may be used, and the slits in the head receiving portion may be fully or partly omitted.

The projections at the locking ring that form a support surface for the rod can also have various other shapes, such as circular, v-shaped, or a flat shape. The projections can also be omitted in some embodiments.

In some embodiments, the head receiving portion can have an inclined open end or can be otherwise asymmetric to allow for a greater angulation of an inserted head in one direction.

The outer surface of the head receiving portion and the inner surface of the locking ring can also have various other shapes that result in compression of the head receiving portion by the locking ring by means of an increasing force when the locking ring is shifted downward. Also the locking ring can have various other designs. For example, the locking ring can be formed without the flexible wall sections.

The extended tabs on the receiving part can be omitted. In addition, in some embodiments, other kinds of locking elements can also be used, for example, non threaded locking elements that have an alternative advancement structure. In addition, all kinds of bone anchoring elements can be used, such as, for example, nails or bone anchors with barbs.

Meanwhile, the use of the instrument has been shown in connection with an already assembled bone anchoring device, it is also contemplated that the instruments can be used for the in-situ placement of a receiving part with a mounted locking ring onto a bone anchoring element that has already been inserted into a bone. In this case, the locking ring would be at an insertion position, and the instrument would be configured to engage the bone anchoring device while the locking ring is at the insertion position. This can be realized, for example, by using an engagement structure in the form of a thread and a design where the tube portions are also rotatable relative to each other.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof

The invention claimed is:

1. A bone anchoring device comprising:
a bone anchoring element comprising a head and a shank;
a receiving part for coupling a rod to the bone anchoring element, the receiving part having a first end, a second end below the first end, a central axis extending between the first and second ends, a rod receiving portion at the first end defining a recess for receiving the rod, the recess extending from the first end towards the second end and forming two free legs, and a head receiving portion at the second end configured to pivotably receive the head of the bone anchoring element; and
a closed ring adjustable relative to the receiving part to exert pressure on the head;
wherein when the closed ring is assembled to the receiving part, the head is insertable into the head receiving portion of the receiving part to a position where at least part of both the receiving part and the closed ring extend below a greatest diameter of the head measured in a direction perpendicular to the central axis; and
wherein when the head of the bone anchoring element is in the head receiving portion, a downwardly facing surface on the receiving part that is closer axially to a bottom of the recess for receiving the rod than to the first end of the receiving part and that is prevented from directly contacting the closed ring forms an abutment to facilitate adjustment of the bone anchoring device to a first configuration, and wherein the bone anchoring device is configured to be held at the first configuration where the closed ring compresses a compressible portion of the bone anchoring device to clamp the head and hold the shank of the bone anchoring element at an angle relative to the central axis of the receiving part while the recess for the rod remains sufficiently unobstructed for the rod to extend and move therethrough.

2. The bone anchoring device of claim 1, wherein the closed ring is positionable around an outside of the receiving part.

3. The bone anchoring device of claim 1, wherein the head is configured to directly engage the receiving part when the head is held in the head receiving portion.

4. The bone anchoring device of claim 1, wherein the closed ring is movable to adjust the bone anchoring device to the first configuration.

5. The bone anchoring device of claim 1, wherein the compressible portion is formed on the receiving part.

6. The bone anchoring device of claim 1, wherein at the first configuration, the head is locked and prevented from moving relative to the receiving part.

7. The bone anchoring device of claim 1, wherein the bone anchoring device is adjustable from the first configuration to a second configuration where the clamping of the head is reduced to adjust the angle of the shank relative to the central axis of the receiving part.

8. The bone anchoring device of claim 7, wherein the closed ring is movable to adjust the bone anchoring device from the first configuration to the second configuration.

9. The bone anchoring device of claim 1, wherein the receiving part defines an opening at the second end for inserting the head of the bone anchoring element into the head receiving portion when the closed ring is assembled to the receiving part.

10. The bone anchoring device of claim 1, wherein the downwardly facing surface is formed on an outer surface of the receiving part.

11. A system comprising:
a bone anchoring device comprising:
a bone anchoring element comprising a head and a shank;
a receiving part for coupling a rod to the bone anchoring element, the receiving part having a first end, a second end below the first end, a central axis extending between the first and second ends, a rod receiving portion at the first end defining a recess for receiving the rod, the recess extending from the first end towards the second end and forming two free legs, a head receiving portion, and an opening at the second end for inserting the head of the bone anchoring element into the head receiving portion to a position where at least part of the receiving part extends below a greatest diameter of the head measured in a direction perpendicular to the central axis; and
a locking member adjustable relative to the receiving part to exert pressure on the head; and
a tool, wherein when the locking member is assembled to the receiving part and the head of the bone anchoring element is in the head receiving portion, the tool is configured to engage and exert respective forces on both the receiving part and the locking member for adjusting the locking member to a first configuration where the head is clamped to hold the shank at an angle relative to the central axis of the receiving part, and from the first configuration to a second configuration where the clamping of the head is reduced to adjust the angle of the shank relative to the central axis of the receiving part, while the recess for the rod remains sufficiently unobstructed for the rod to extend and move therethrough.

12. The system of claim 11, wherein the locking member is positionable around an outside of the receiving part.

13. The system of claim 11, wherein the head is configured to directly engage the receiving part when the head is held in the head receiving portion.

14. The system of claim 11, wherein the locking member is configured to compress the head receiving portion to clamp the head.

15. The system of claim 11, wherein at the first configuration, the head is locked and prevented from moving relative to the receiving part.

16. The system of claim 11, wherein when the locking member is adjusted to the first configuration by the tool and the tool is separated from the bone anchoring device, the locking member is configured to be held at the first configuration.

17. A bone anchoring device comprising:
a bone anchoring element comprising a head and a shank;
a receiving part for coupling a rod to the bone anchoring element, the receiving part having a first end, a second end below the first end, a central axis extending between the first and second ends, a rod receiving portion at the first end defining a recess for receiving the rod, the recess extending from the first end towards the second end and forming two free legs, a head receiving portion, and an opening at the second end for inserting the head of the bone anchoring element into the head receiving portion to a position where at least part of the receiving part extends below a greatest diameter of the head measured in a direction perpendicular to the central axis; and
a locking member adjustable relative to the receiving part to exert pressure on the head;
wherein when the locking member is assembled to the receiving part and the head of the bone anchoring element is in the head receiving portion, a downwardly facing surface on the receiving part that is closer axially to a bottom of the recess for receiving the rod than to the first end of the receiving part and that is prevented from directly contacting the locking member forms an abutment to facilitate adjustment of the locking member to a first configuration, and wherein the locking member is configured to be held at the first configuration where a compressible portion of the bone anchoring device is compressed to clamp the head and hold the shank at an angle relative to the central axis of the receiving part, and is adjustable from the first configuration to a second configuration where the compression of the compressible portion is reduced to adjust the angle of the shank relative to the central axis of the receiving part, while the recess for the rod remains sufficiently unobstructed for the rod to extend and move therethrough.

18. The bone anchoring device of claim 17, wherein the locking member is positionable around an outside of the receiving part.

19. The bone anchoring device of claim 17, wherein the head is configured to directly engage the receiving part when the head is held in the head receiving portion.

20. The bone anchoring device of claim 17, wherein the locking member is configured to compress the head receiving portion to clamp the head.

21. The bone anchoring device of claim 17, wherein at the first configuration, the head is locked and prevented from moving relative to the receiving part.

* * * * *

UNITED STATES PATENT AND TRADEMARK OFFICE
CERTIFICATE OF CORRECTION

PATENT NO. : 12,029,452 B2
APPLICATION NO. : 17/841238
DATED : July 9, 2024
INVENTOR(S) : Timo Biedermann et al.

It is certified that error appears in the above-identified patent and that said Letters Patent is hereby corrected as shown below:

In the Specification

In Column 7, Line 60, delete "poly-1-lactide" and insert -- poly-l-lactide --.

In Column 12, Line 22, after "thereof" insert -- . --.

Signed and Sealed this
Twenty-second Day of October, 2024

Katherine Kelly Vidal
*Director of the United States Patent and Trademark Office*